United States Patent
Düering (10) Patent No.: US 9,358,386 B2
(45) Date of Patent: Jun. 7, 2016

(54) MEDICAL DEVICE FOR INSERTION INTO THE HUMAN OR ANIMAL BODY

(71) Applicant: MARVIS MEDICAL GMBH, Frechen (DE)

(72) Inventor: Klaus Düering, Frechen (DE)

(73) Assignee: MARVIS MEDICAL GMBH, Frechen (DE)

( * ) Notice: Subject to any disclaimer, the term of this patent is extended or adjusted under 35 U.S.C. 154(b) by 129 days.

(21) Appl. No.: 14/346,644

(22) PCT Filed: Sep. 21, 2012

(86) PCT No.: PCT/EP2012/003963
§ 371 (c)(1),
(2) Date: Mar. 21, 2014

(87) PCT Pub. No.: WO2013/041235
PCT Pub. Date: Mar. 28, 2013

(65) Prior Publication Data
US 2014/0221818 A1 Aug. 7, 2014

Related U.S. Application Data

(60) Provisional application No. 61/537,685, filed on Sep. 22, 2011.

(30) Foreign Application Priority Data

Sep. 21, 2011 (DE) .......................... 10 2011 113 816

(51) Int. Cl.
*A61B 5/05* (2006.01)
*A61N 1/05* (2006.01)
(Continued)

(52) U.S. Cl.
CPC .............. *A61N 1/0587* (2013.01); *A61B 5/066* (2013.01); *A61N 1/05* (2013.01); *A61N 5/1007* (2013.01); *A61B 2017/00469* (2013.01); *A61N 2001/086* (2013.01)

(58) Field of Classification Search
CPC .......... A61B 5/055; A61B 6/00; A61B 5/064; A61B 6/504
See application file for complete search history.

(56) References Cited

U.S. PATENT DOCUMENTS 6,844,492 B1 * 1/2005 Wang ..................... B82Y 25/00
174/36
2003/0208142 A1 * 11/2003 Boudewijn ............. A61B 5/064
600/585
(Continued)

FOREIGN PATENT DOCUMENTS

CN 102036695 A 4/2011
DE 3417479 A1 11/1985
(Continued)

*Primary Examiner* — Joel Lamprecht
(74) *Attorney, Agent, or Firm* — Hultquist, PLLC; Steven J. Hultquist; Mary B. Grant (57) ABSTRACT

A medical device according to the invention for insertion into a human and/or animal body comprises an elongated tubular lead probe including a proximal end portion and a distal end portion, an opening which opens into a lumen extending in the axial direction being formed on the proximal end of the lead probe, and the distal end of the lead probe being closed. The medical device further comprises an elongated core which is constructed in such a manner that it can be inserted into the lead probe and removed again via the lumen, and the core is made from non-metallic filaments and a matrix material.

20 Claims, 4 Drawing Sheets (51) Int. Cl.
*A61B 5/06* (2006.01)
*A61N 5/10* (2006.01)
*A61B 17/00* (2006.01)
*A61N 1/08* (2006.01)

(56) References Cited

U.S. PATENT DOCUMENTS

2003/0229277 A1 12/2003 Kolberg et al.
2005/0149002 A1* 7/2005 Wang ............... A61L 29/18
  606/1
2008/0312597 A1* 12/2008 Uihlein ............. A61M 25/09
  604/164.13
2010/0063379 A1 3/2010 Pfeffer et al.
2011/0166439 A1* 7/2011 Pfeffer ............. A61L 27/50
  600/411

FOREIGN PATENT DOCUMENTS

| | | |
|---|---|---|
| DE | 3526738 A1 | 2/1987 |
| DE | 4124606 A1 | 1/1993 |
| DE | 102005022688 A1 | 11/2006 |
| EP | 1356845 A1 | 10/2003 |
| EP | 2450067 A1 | 5/2012 |
| WO | 2007000148 A2 | 1/2007 |
| WO | 2009141165 A2 | 11/2009 |

* cited by examiner

MEDICAL DEVICE FOR INSERTION INTO THE HUMAN OR ANIMAL BODY

CROSS-REFERENCE TO RELATED APPLICATIONS

This application is a U.S. national phase under the provisions of 35 U.S.C. §371 of International Patent Application No. PCT/EP12/03963 filed Sep. 21, 2012, which in turn claims priority of German Patent Application No. 102011113816.5 filed Sep. 21, 2011 and the benefit of U.S. Provisional Patent Application No. 61/537,685 filed on Sep. 22, 2011. The disclosures of such international patent application, German priority patent application, and U.S. provisional patent application are hereby incorporated herein by reference in their respective entireties, for all purposes.

The present invention relates to a medical device for insertion into the human or animal body.

EP 1 356 845 D1 discloses a catheter. This catheter comprises a catheter shaft in which an axially continuous, central lumen is provided. A coiled supply line for a ring electrode extends in a wall of the catheter shaft; said ring electrode is arranged in an isolating head body which forms the distal end of the catheter. Further, the catheter comprises a mandrin sleeve extending in a lumen and a guide wire extending in the mandrin sleeve. The guide wire can be led out through a lock opening at the distal end of the catheter. Proximally in front of the lock opening, a sealing unit which can be reversibly pierced by the mandrin sleeve is provided for sealing off the lumen.

Pacemaker probes are advanced vascularly by puncture of a blood vessel up to the heart and positioned there. For positioning, either a guide wire or a mandrin is used. Usually, the guide wire is inserted in the axial direction toward the distal end, so that the catheter of the pacemaker probe can be pushed via the guide wire. In doing so, the distal end of the catheter is open to such an extent that the guide wire can exit the catheter. If a mandrin is used, the distal end of the catheter is closed. The mandrin is provided with a ball or the like at the distal end, so that the distal end of the pacemaker probe cannot be pierced and the heart tissue cannot be injured. Further, the tip of the pacemaker probe may be provided with X-ray markers to allow for a control of the positioning by means of X-ray imaging technology. X-ray imaging technology does not allow to produce a direct image of the heart. This is only possible with the aid of a contrast agent modeling the blood flow. Thus, the only way to find a suitable positioning for the pacemaker probe in the heart wall is the dissipation of electric current into the heart, so that it will not be arranged in necrotic tissue. As a consequence, it is usual that several, in many cases 6 to 8 attempts are required for positioning a pacemaker probe in the heart wall, until a suitable position has been found. With every positioning attempt and the subsequent withdrawal of the pacemaker probe, the heart wall is slightly injured.

The computer tomography (CT) allows for the imaging of soft tissue by means of a layer-wise imaging with X-rays, so that the positioning can be monitored better. However, the exposure to radiation is quite high in this case.

Cardiac pacemakers which are compatible to magnetic resonance tomography (MRT) are commercially available (e.g. from the companies Biotronik and Medtronic). In order to not impair the functionality of the cardiac pacemaker by MRT, magnetically chargeable parts in the cardiac pacemaker have been replaced and circuits have been shielded. However, these MRT compatible cardiac pacemakers and pacemaker probes cannot be inserted under MRT control, because either an MRT compatible guide wire or an MRT compatible mandrin is required for this purpose. The current mandrins of metal are dangerous in MRT because of electrical conductivity and heating. Patients who have received an MRT compatible cardiac pacemaker are allowed to undergo an MRT examination not until several weeks after its implantation.

The positioning of cardiac pacemaker probes would be made possible under MRT imaging in one step, which is due to the clear representation of the heart wall tissue and the necrotic spots where the pacemaker probes must not be placed, as there is no heart muscle activity and electrical perceptivity at those places any more. This would imply that the heart wall tissue is well protected in a patient-friendly manner and the duration of the process of placing the pacemaker probe is considerably reduced. The same applies to defibrillators, for example, for which it is also required to place the probes.

The brachytherapy is a form of the radiation therapy in which a radiation source is placed in the body within or in direct vicinity of the area which is to be treated with radiotherapy. The brachytherapy is frequently used as an effective treatment method for cancerous diseases of the uterine cervix, prostate, chest and skin. It may also be used for tumor treatments on numerous other body areas. In brachytherapy, radiation sources, in particular Iridium, which are arranged on the tip of an insertion rod, are inserted in a distally closed applicator so that the radiation source does not contact the tumor itself, but can be specifically positioned centrally in the tumor. By means of imaging methods, the best possible placement in the tumor is determined and reached. For the determination of radiation doses required for the therapy, it is usual to repeatedly measure the position, nowadays usually under X-ray imaging. The visualization of tumors, however, can be reached much better and more precise by MRT in very many cases, as MRT offers a far more better representation of the soft tissue and a much higher soft part contrast.

WO 2007/000148 A2 shows a rod-shaped body which serves for forming medical instruments such as of catheters or guide wires for catheters. This rod-shaped body consists of one or more filaments and a non-ferromagnetic matrix material which encloses the filaments. The matrix material has received a doping of particles which produce artifacts under magnetic resonance tomography.

WO 2009/141165 describes a medical instrument which can be inserted into a human or animal body and comprises an instrument body. The instrument body includes at least one rod-shaped body which has a low electrical conductivity and is formed from a matrix material and non-metallic filaments. This medical instrument is distinguished in that the rod-shaped body is doped with an X-ray marker, and the medical instrument comprises an MRT marker.

DE 3 417 479 A1 shows a venous catheter comprising a guide mandrin for ECG inspection. The guide mandrin consists of an electrically conductive metal wire with a plastic sheathing.

DE 35 26 738 C2 discloses a device for checking the position of a central venous catheter. Here, a mandrin is used which consists of a metal strand and is wrapped in plastic.

DE 41 24 606 A1 describes a mandrin formed from a metal spiral.

DE 10 2005 022 688 A1 relates to a guide wire comprising a jacket which has a higher rigidity than a core arranged therein.

It is the object of the present invention to provide a medical device which can be arranged at a predetermined site in the human body.

It is another object of the present invention to provide a medical device whose flexural rigidity can be altered.

It is a further object of the present invention to provide a medical device which can be made visible by means of MRT during inserting or positioning it in the human and/or animal body.

One or more of the above-mentioned objects are achieved by the features set forth in the claims.

A medical device according to the invention for insertion into a human and/or animal body comprises an elongated, tubular lead probe including a proximal end portion and a distal end portion, an opening which opens into a lumen extending in the axial direction being formed on the proximal end of the lead probe, and the distal end of the lead probe being closed. The medical device further comprises an elongated core which is constructed in such a manner that it can be inserted into the lead probe and removed again via the lumen, and the core is made from non-metallic filaments and a matrix material.

In the context of the present invention, a lead probe is to be understood as an elongated tubular body which can be inserted into a human or animal body and is designed for receiving a core. A lead probe of this type is part of a pacemaker probe, for example, or may be designed as a hose or cannula which is used as an applicator for brachytherapy.

If the medical device is realized as a pacemaker probe, the lead probe is correspondingly implemented as a flexible or rigid hose or catheter.

If the medical device is intended for use in brachytherapy, the lead probe is correspondingly realized as an applicator, for example as a rigid cannula or a flexible plastic hose for brachytherapy.

In the context of the present invention, a core is to be understood as an elongated rod-shaped compound element which can be inserted into a lead probe. The core may be formed from non-metallic filaments which are enclosed by a matrix material. Optionally, marker particles may be embedded in the matrix material for the visualization of the core. The matrix material preferably is a plastic material such as epoxy resin, PEEK, PEBAX, PE, PP, PU, silicone, polylactic acid polymers. The filaments, for instance, are glass fibers, ceramic fibers, Dacron®, aramide, polyaramide, Kevlar®, Dyneema® or vegetable fibers (such as silk, sisal, hemp, etc.).

The pacemaker probes and defibrillator probes which are known from prior art usually comprise a guide wire or a mandrin.

The guide wires are frequently provided with a metallic core and the mandrins are usually made of stainless steel or any other metal. This is why they are not MRT compatible.

The medical device according to the invention provides a closed system comprising a lead probe with a lumen in which a core realized as a plastic body is movably arranged, so that the medical device is compatible and safe with respect to MRT technology.

The diameter of the core preferably amounts to approximately 70% to 95% of the diameter of the lumen of the lead probe. The remaining annular gap between the core and the lead probe which is filled with air is so small that it does not create any interfering artifacts (black spots in the image) during visualization by means of MRT.

The inventor has surprisingly found out that a small air gap between the core and the lead probe, i.e. the concomitant residual volume of air in the medical device, does not affect or disturb the MRT imaging process. It was not possible to detect any artifacts which are due to said circumstance.

The core preferably has a higher flexural rigidity than the lead probe. This is why the flexural rigidity of the lead probe can be altered to a large extent by the axial position of the core in the lead probe.

By providing a medical device implemented in the form of a pacemaker probe and made of a flexible or soft lead probe with an electrode arranged thereon and a core arranged in the lead probe which has a higher flexural rigidity than the lead probe, it is possible to adapt the distal end of the medical device to the geometry of the vascular walls during the inserting and positioning processes and to selectively approach the target position in the tissue. The lead probe can be erected or stiffened by the core, in order to position the pacemaker probe specifically in the healthy heart wall tissue.

The same also applies to a medical device for brachytherapy, whose lead probe has the features as described above. In this case, the lead probe is deliberately guided into the tumor tissue by means of the core.

It is preferred that the core comprises an MRT marker which extends in particular over a major part of the length of the core. The MRT marker allows to detect the position of the medical device in the human or animal body.

This makes it possible to work under permanent visual control in the MRT during the implantation of the pacemaker or defibrillator. In this way, the scarred tissue can be distinguished from the healthy tissue so as to localize healthy tissue for the insertion of the pacemaker probe.

If a lead probe designed for brachytherapy, e.g. implemented as a rigid cannula, comprises a core which is provided with MRT markers, it is possible to work under permanent visual control in the MRT during the implantation of the lead probe. In this way, the tumor tissue can be distinguished from the healthy tissue, in order to localize the tumor tissue for the insertion of the radiation source. Here, the tumor tissue may be situated in a body cavity, e.g. the uterine cervix, uterus or vagina, in a body lumen such as e.g. the trachea or esophagus or even in a blood vessel. In these cases, the lead probe is inserted through the body cavity or body lumen. In other cases, for instance with tumors in an organ such as liver or kidney, the lead probe is interstitially guided through the skin and the tissue to the tumor.

It the lead probe is positioned in the area of the tumor tissue, the core can be removed and instead of the core a radiation source is inserted into the lead probe. In this way, the radiation source can be positioned in direct vicinity of the tumor tissue or directly in the tumor tissue, so that the smallest possible amount of healthy tissue is damaged during the radiation therapy.

It is advantageous in brachytherapy that the tissue can be analyzed under magnetic resonance tomography by pulling out the core from the lead probe, without an MRT artifact being produced which might locally superimpose the target tissue and hence impair the precision of the target control. By repeatedly pulling out the core and pushing it back again in parts, it is very easy to take MRT images in alternating manner for the visualization of the applicator and of the tumor. A fixedly attached MRT marker does not offer such advantage.

In the event that the air volume in the lead probe produces a disturbing air-related artifact superimposing the tissue when the core together with the MRT marker has been removed, it is possible to insert another core without any MRT markers, which eliminates the air-related artifact. In case a lead probe is used which consists only of plastic and does not produce an artifact of its own (except for the displacement artifact), a distinct artifact can be produced in the MRT for the precise localization of the medical device or an image at the position of the medical device which is (virtually) free from any artifacts, as required, by changing between a core with MRT markers and a core without MRT markers.

Furthermore, provision can be made to provide the medical device with a core which has a higher flexural rigidity than the lead probe and also comprises MRT markers.

In this way, a combination of the above advantages is achieved.

To give an example, the process of inserting a pacemaker probe can be monitored if the pacemaker probe itself does not produce a reliable MRT artifact or no reproducible reliable MRT artifact. Subsequently, the distal end of the pacemaker probe can be erected or stiffened in the area of the healthy tissue by the core and hence can be exactly positioned.

Due to the variable flexural rigidity, a medical device for brachytherapy can be adapted to the geometry of the cavity walls during inserting and positioning it and can be visually monitored by means of the MRT markers until it is arranged in the tumor tissue. If the distal end of the medical device is situated in the vicinity of the tumor tissue or in the tumor tissue, it can be erected or stiffened by the core and exactly positioned in this way.

The invention will be explained in more detail below with the aid of the exemplary embodiments illustrated in the drawings in which.

Preferred embodiments of the present invention will be described in the following.

Figure 1:
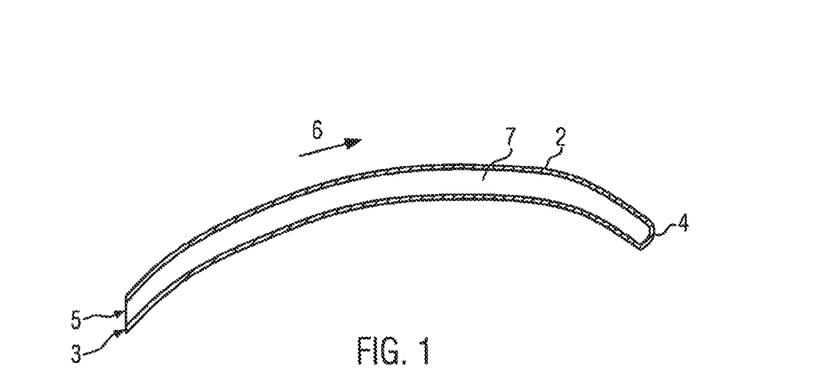
FIG. 1 shows a lead probe in a lateral section view.
Figure 2:
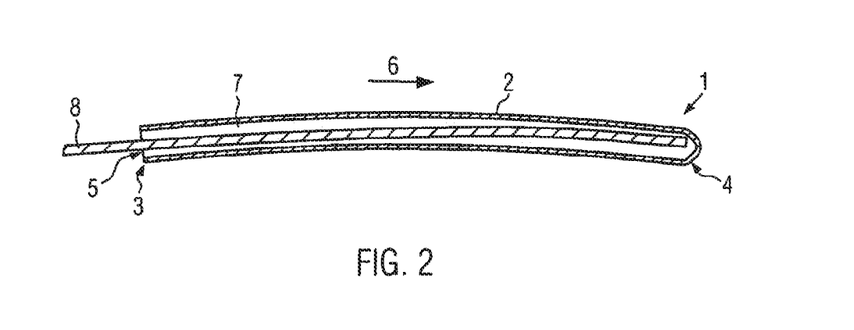
FIG. 2 shows a lead probe with a core arranged therein, in a lateral section view.

A medical device 1 according to the invention for insertion into the human and/or animal body comprises an elongated, tubular lead probe 2 having a proximal 3 end portion and a distal end portion 4, an opening 5 which opens into a lumen 7 extending in the axial direction 6 being formed on the proximal end 3 of the lead probe 2, and the distal end of the lead probe 2 is closed. Further, the medical device 1 comprises an elongated core 8 which is designed such that it can be inserted into the lead probe 2 and again removed via the lumen 7, and the core 8 is formed from non-metallic filaments 9 and a matrix material 10.

In the following, the various embodiments of a core according to the invention will be described.

The core 8 comprises at least one elongated, rod-shaped compound element 13 which is formed from glass fiber bundles 12 or glass fiber rovings embedded in a matrix material such as epoxy resin, for example. By providing the glass fibers 12, a core 8 is made available which has a high bending and torsional stiffness.

The fibers preferably extend over a major part of the length of the core 8 and in particular over the entire length of the core 8. They extend in the core 8 preferably so as to be substantially parallel.

Furthermore, the core may also contain aramide fibers 11 in addition to the glass fibers 12. The aramide fibers 11 provide for a high tear strength of the core 8.

The higher the amount of the glass fibers 12 in the core 8, the higher is the stiffness and the flexural rigidity of the core 8.

Figure 3:
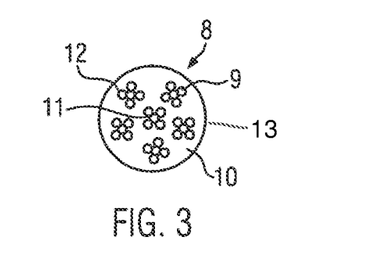
FIG. 3 shows a cross-section of a core made of non-metallic filaments which are enclosed by a matrix material.

A core 8 may be formed, for instance, from a central 11Tex aramide fiber roving 11 and five 33Tex glass fiber rovings 12 concentrically surrounding the central aramide fiber roving 11 and equidistantly spaced from each other (FIG. 3). Instead of rovings, yarns may also be used, but rovings are preferred as higher strengths can be achieved with smaller diameters. A core having such a design has an outer diameter of 0.35 mm to 0.38 mm.

As an alternative, it would also be possible to use 6.1Tex aramide fiber rovings instead of the 11Tex aramide fiber rovings. A core of such design has an outer diameter of approximately 0.34 mm to 0.36 mm.

In another embodiment, also a central 22Tex aramide fiber roving can be used instead of the 11Tex aramide fiber roving, which is concentrically surrounded by seven 33Tex glass fiber rovings which are equidistantly spaced. A core with such a design has an outer diameter of 0.42 to 0.45 mm.

In a further embodiment, the core 8 having a diameter of approximately 0.35 mm to 0.38 mm may contain about 200Tex glass fibers which are incorporated in the form of three 66Tex glass fiber rovings.

It goes without saying that compound elements 13 having a larger diameter and higher strength can be manufactured by use of a larger amount of epoxy resin and a higher number of fibers.

The compound element 13 can be constructed according to the rod-shaped bodies which are described in WO 2009/141165 or WO 2007/000148 A2 to which reference is made to their full extent.

The surface of the core might comprise outwardly projecting glass fibers or other non-metallic filaments which could impair the safety of the product. In order to obtain a smooth surface without any protruding filaments, the core can be manufactured so as to have a somewhat larger diameter than the target diameter and then be ground off to the target diameter. Grinding the surface down to the target diameter also results in a higher flexibility in production, as standard glass fiber and aramide rovings only allow to obtain specific geometries and achieve certain resultant outer diameters. Customary rovings are available only in specific diameters. If a rod-shaped body having a diameter between the standard sizes of two rovings is manufactured without grinding, it has an external layer which consists exclusively of matrix material and is not reinforced by non-metallic filaments. This is not ideal, because the strength of the outer layer has a particularly high impact on the stiffness of the entire rod-shaped body. The diameter of a rod-shaped body makes an impact on its stiffness by the fourth power.

Grinding allows for the manufacture of rod-shaped bodies with any fine increments and non-metallic filaments which are uniformly distributed over the entire cross-sectional area. The ratio between the cross-sectional areas of non-metallic filaments and the matrix material, in particular the epoxy resin, is preferably 60:40; these values may vary by ±10.

Figure 4:
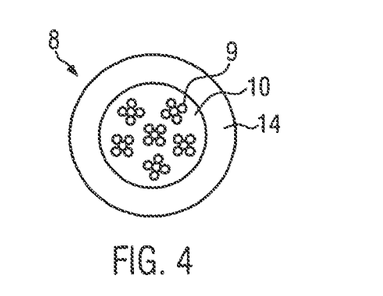
FIG. 4 is a cross-section of the core shown in FIG. 3, including a cladding matrix.

In order to increase the diameter of the core 8 or to reduce the air gap between the outer wall of the core and the inner wall of the lead probe 2, provision can be made to encase the cores outlined above with a cladding matrix 14 (FIG. 4). The cladding matrix is formed from PU, for example.

Figure 5:
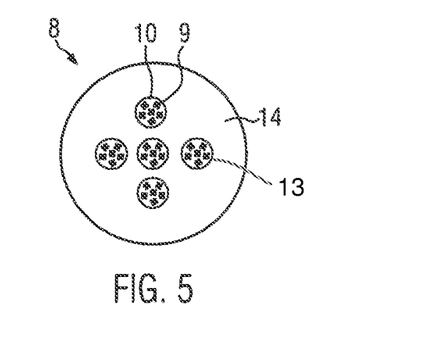
FIG. 5 shows a cross-section of a core made up of several compound elements embedded in a cladding matrix.

A core 8 may also be designed such that several compound elements 13 as outlined above are embedded in a cladding matrix 14 (FIG. 5). Optionally, marker particles can be embedded in the matrix material and/or in the cladding matrix for the visualization of the core 8 by means of MRT. It is preferred that iron microparticles are embedded as MRT markers in the matrix material 10 made of epoxy resin.

The lower limit for the size of the iron microparticles is at least 1 μm or 10 μm and 20 μm or 30 μm and 40 μm. In general, the larger the particles, the more pronounced are the artifacts generated by them and the better is their visibility under MRT. The upper limit of the size of the iron microparticles is less than 150 μm or 100 μm or 80 μm or 70 μm or 60 μm. For large particle sizes of approximately 100 μm and more, processing is more difficult and it is not easy to distribute them uniformly in the matrix material. The size of the microparticles is preferably in a range between 20 μm and 70 μm and particularly preferred between 40 and 60 μm.

In addition to the MRT marker particles contained in the matrix material and/or in the cladding matrix, it is also possible to apply a separate MRT tip marker at the distal end portion of the core, which creates a wider artifact in the MRT image, e.g. having the double or threefold width of the artifact over the entire length of the core. Having such a tip marker, the tip of the core and hence the distal end of the medical device can be clearly identified in the MRT image. If the tip marker can not be seen in the MRT image, the tip is not situated in the visualized layer of the MR image and the layer adjustment has to be readjusted.

The MRT tip marker is applied, for instance, by applying a self-curing polymer solution containing MRT marker particles. After the curing process, the polymer solution forms a layer which extends preferably over a longitudinal region of some μm up to some mm. The layer may be only applied to an end face of the rod-shaped body, so that the longitudinal extent corresponds to the layer thickness. The layer, however, may also be applied on the lateral surface of the rod-shaped body, with the longitudinal extent being preferably not longer than 5 mm and in particular not longer than 3 mm. The polymer solution may consist of PEBAX, for example. All MR markers which are disclosed herein may be used as MRT marker particles, but iron marker particles are preferred.

The tip marker may be provided in addition to MRT markers of the core, so that it creates a more pronounced artifact in the region of the tip than in the remaining region of the core in an MRT imaging method.

The alternating use of unmarked cores, of only continuously marked cores and of continuously marked and tip-marked cores allows for the highest possible flexibility for the exact and ideal positioning of the medical device on or in the target tissue under permanent MRT visual control.

The cross-section of the core 8 preferably has an approximate circular shape, as the lumen 7 of the lead probe 2 is also circular. The inner diameter of the lumen 7 of the lead probe 2 is preferably only slightly larger than the outer diameter of the core 8, so that the latter can be pushed through the lead probe 2 almost without any friction and merely a minimum air gap is formed between the outer surface of the core 8 and the inner surface of the lead probe 2.

The diameter of the core 8 amounts to approximately 60% to 98% or 70% to 95% or 80% to 90% of the diameter of the lumen 7 of the lead probe 2. Here, it is important that the surface of the core 8 and in particular its distal tip glide easily through the lumen 7 of the lead probe 2. To this end, the distal tip can be rounded according to the methods known from prior art. Further, the core 8 has a mostly homogenous stiffness from the proximal end 3 to the distal end 4. In an alternative embodiment, the distal end of the core 8 may have a decreasing stiffness. This can be achieved by grinding the core body, with the result of a reduction of the outer diameter in said portion.

In the following, various embodiments of the medical device 1 comprising a lead probe 2 and a core 8 and intended for insertion into a human or animal body will be described.

According to a first exemplary embodiment of the present invention, the medical device 1 is realized as a pacemaker probe which is provided with a corresponding electrode (not illustrated) for cardiac pacemakers or defibrillators, with the lead probe 2 forming a tube-shaped catheter whose distal end 4 has a corresponding electrode attached to it. Such a lead probe 2 is realized so as to be soft and flexible. The core 8 which can be arranged in the lead probe 2 is designed such that it has a higher flexural rigidity than the lead probe 2. To this end, a core 8 is used which has a maximum proportion of glass fiber bundles, as these ensure a high flexural rigidity. Preferably, the core also comprises aramide fibers providing for a high tear strength.

This allows to adapt the distal end 4 of the medical device 1 to the geometry of the vascular walls during insertion and positioning and to move it close to healthy heart wall tissue.

As the diameter of the lumen 7 of such a lead probe 2 typically amounts to approximately 0.4 mm, the diameter of the core 8 has to be correspondingly adapted. A core 8 of this type preferably consists of only the rod-shaped compound element 13 without the cladding matrix 14 (see FIG. 3).

The flexural rigidity of the medical device 1 can be changed by shifting the core 8 in the axial direction with respect to the lead probe 2, to selectively position the pacemaker probe in the healthy heart wall tissue.

According to a further embodiment of the medical device, the flexural rigidity of the core 8 is approximately equal to the flexural rigidity of the lead probe 2, or is also somewhat smaller than that of the lead probe 2. According to this exemplary embodiment, the core 8 is provided with MRT markers which extend in particular over a major part of the length of the core 8 or over the entire length of the core 8. The MRT markers allow to detect the position of the medical device 1 in the human or animal body. The core 8 may comprise glass fibers. In addition to the glass fibers or also as an alternative to the glass fibers, the core may comprise aramide fibers giving the core a higher tear strength.

This makes it possible to work under permanent visual control in the MRT during the implantation of the pacemaker or defibrillator probes. In this way, the lead probe 2 can be selectively and safely placed in healthy tissue in the heart wall, so that a misplacement in scarred tissue and a resultant required repositioning are avoided. Thus, the medical device 1 can be correctly placed usually in one working process.

According to a further embodiment of the present invention, the core 8 has a higher flexural rigidity than the lead probe 2 and comprises MRT markers, too.

This results in a combination of the advantages outlined above. In this way, it is possible to work under permanent visual control in the MRT during the implantation of the pacemaker or defibrillator probe and to simultaneously adapt the flexural rigidity of the lead probe 2 in accordance with the bends of the vascular walls. It is possible in this way to follow the bends of the blood vessels and to finally detect the healthy heart wall tissue. Then, the distal end of the lead probe 2 can be made stiff in order to selectively arrange the pacemaker probe in the healthy heart wall tissue.

A rigid core 8 allows for the use of a very flexible lead probe 2. This is especially advantageous if the lead probe 2 is implanted in the human body on a permanent basis. The more flexible the lead probe 2, the better is its adaptation to the body geometry or vessel geometry and its ability to take part in any body movements. The core preferably comprises glass fibers and aramide fibers.

According to further embodiment of the present invention, the medical device 1 is designed for brachytherapy. In this case, the lead probe 2 is preferably designed either as a flexible hose or as a rigid cannula.

A rigid cannula is provided, for example, with tumors in an organ such as the liver or kidney. Here, the lead probe is guided to the tumor interstitially through the skin and the tissue.

A flexible hose is provided in particular if the tumor tissue is situated in a body cavity, e.g. in the uterine cervix, uterus or vagina or in a body lumen such as the trachea or esophagus or even in a blood vessel.

Due to the fact that the work can be performed under permanent visual control in the MRT, the insertion process is substantially facilitated and the tumor tissue can be localized.

According to a first embodiment of a medical device for brachytherapy, the lead probe is designed as a rigid cannula. Further, a core is provided which is equipped with MRT markers. This allows to work under permanent visual control in the MRT during the implantation of the lead probe. In this way, it is possible to distinguish the tumor tissue from any healthy tissue in order to localize the tumor tissue for the insertion of the radiation source.

Here, the stiffness of the core plays a minor role. It is advantageous, however, if the core comprises aramide fibers which ensure a high tear strength, so that the core does not tear during manipulation even with high tensile stress.

If the lead probe is arranged in the area of the tumor tissue, the core can be removed and a radiation source is inserted into the lead probe in lieu thereof. The radiation source is preferably formed from iridium. Thus, the medical device according to the invention makes it possible to arrange the radiation source in direct vicinity of the tumor tissue or directly in the tumor tissue, so that the smallest possible amount of healthy tissue is damaged during the radiation therapy.

The lead probe of a medical device for brachytherapy comprises a lumen with a diameter of approximately 0.8 mm to 1.5 mm. The diameter of the core has to be correspondingly adapted.

Having such a diameter, the core can be formed from one or more rod-shaped compound elements which can be embedded in a cladding matrix.

According to a second embodiment of a medical device for brachytherapy, the lead probe is designed as a flexible hose. Unless otherwise specified, the medical device comprises the features of the first embodiment for brachytherapy.

The core which can be arranged in the lead probe is designed here such that it has a lower, an identical or a higher flexural rigidity than the lead probe. To this end, a core 8 is used which has a lower or higher proportion of glass fiber bundles, where a higher proportion of glass fiber bundles results in a higher flexural rigidity. It is preferred that the core 8 also comprises aramide fibers, giving it a high tear strength.

Due to the changeable flexural rigidity of the medical device, the latter can be adapted to the geometry of the cavities during inserting and positioning it.

According to the invention, any combinations between flexible to hard lead probes and cores are conceivable, with these cores having a higher, an identical or a lower flexural rigidity than the lead probe and comprising marker particles for the MRT or X-ray visualization or no marker particles at all. Here, reference is made to FIGS. 3 to 6 disclosing corresponding cores for the respective case of application by way of example.

Figure 6:
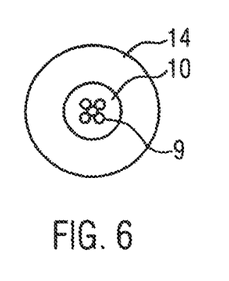
FIG. 6 shows a cross-section of a core which is formed from one compound element embedded in a cladding matrix.
Figure 7:
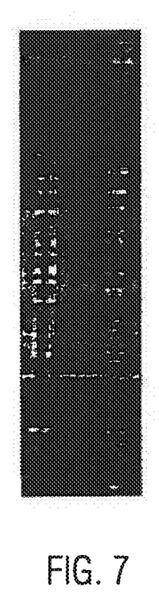
FIG. 7 shows images of a test equipment, which have been created by means of magnetic resonance tomography.
Figure 8:
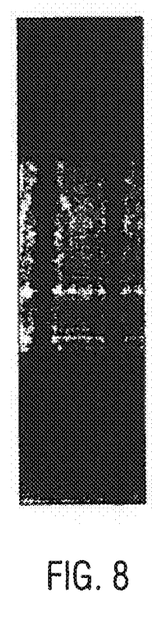
FIG. 8 shows images of a test equipment, which have been created by means of magnetic resonance tomography.
Figure 9:
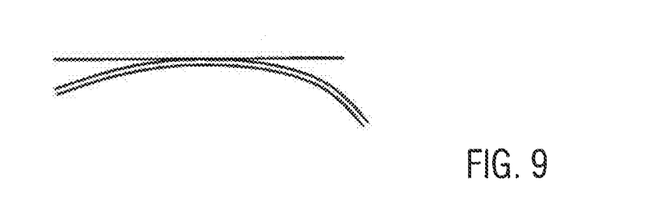
FIG. 9 shows a lead probe without a core, in a side view.
Figure 10:
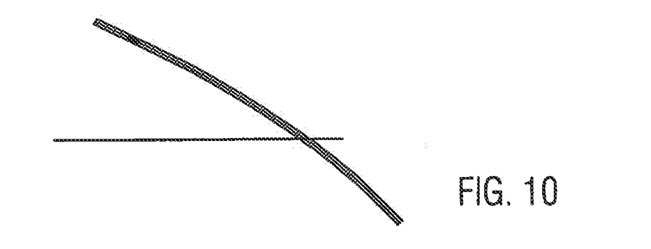
FIG. 10 shows a lead probe comprising a stainless steel mandrin according to prior art, in a side view.
Figure 11:
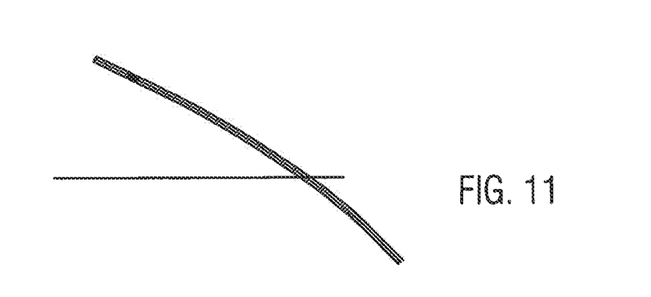
FIG. 11 shows a lead probe comprising a core according to the invention.

If it is not necessary for the core to provide stiffness for the medical device, it may comprise merely one single compound element (FIG. 6). The compound element is surrounded by a cladding matrix, in order to be adapted to the inner diameter of the lead probe. The compound element is preferably concentrically arranged in the core in the area of its longitudinal axis, if it comprises MRT markers, so that the MRT markers are situated in a narrow area around the longitudinal axis of the core. In the imaging process, the MRT markers produce artifacts which extend beyond the area of the object itself if conventional MRT sequences are used for image generation. In this embodiment in which the MRT markers are concentrated in the center of the core, the artifacts are as small as physically possible, as the distance to the surrounding water molecules which are imaged in the MRT is as large as possible. This is why the core can be identified very well and in a locally limited manner, on the one hand, but is bordered to such an extent that the representation of the adjoining tissue is not affected. Due to the fact that the marker particles are concentrated in the center of the core and because of the distance to the surrounding water molecules in the body existing due to the annular gap filled with air and the lead probe wall, an artifact is obtained which is as bordered as possible and hence optimized for the pinpoint approach to the tumor.

In case of using several compound elements, it may be expedient for this reason to only dope the central compound element with MRT markers.

With respect to doping with MRT markers, reference is made to the corresponding text passages of EP 101 878 63 which is referred to in its full extent. In case of doping with MRT markers, the targets are to a) obtain a pronounced and b) a locally delimited and sharp artifact. The more pronounced the artifact, the larger is its width. It is preferred that the artifact is sufficiently intense in the direction parallel to the main magnetic field and not too wide in the orthogonal direction, while these parameters should be correspondingly balanced.

The following effects have an influence on the intensity and the width of the artifacts of the medical device comprising a lead probe and a core:

The higher the concentration of the MRT markers, the more pronounced and wider is the artifact.

The larger the particles, the better the balance between the imaging processes in parallel and orthogonal directions. Nevertheless, the distribution of the particles may become uneven in the event of excessively large particles, so that a uniform artifact is not obtained any longer. The size of the particles is limited by the manufacturing process of the compound elements (rod-shaped bodies) and/or the medical device. Particles with an excessively large size can no longer pass through the manufacturing tools. The most suitable particle sizes are in the range between 1 µm and 150 µm. The particles preferably have a size of at least 1 µm, 2 µm, 5 µm, 10 µm, 20 µm, 30 µm, 40 µm or 50 µm. Good results are also achieved with particles which have been sieved with a screen with a mesh width of 150 µm. A screen with a mesh width of approximately 80 µm to 130 µm is also suitable. It is particularly preferred that the iron particles have a size from 20 to 100 µm, more preferably from 30 to 80 µm and most preferably from 40 to 65 µm.

A higher number of doped compound elements results in a more pronounced artifact than a single compound element with the same or even a higher amount of marker particles.

The size and in particular the width of the tip marker artifact depends on the absolute applied amount of the MRT marker.

The distance from the marker particles or the compound elements to surrounding water molecules has an influence on the sharpness and intensity of the artifact. The larger the distance between the marker particles and the surrounding water molecules, the weaker is the influence of the magnetic field on these water molecules. In other words, the larger the diameter of the medical device in relation to the diameter of the concentrically arranged compound element 13 doped with MRT marker particles, the more limited is the created artifact and the sharper is the resultant image of the medical device in the MRT image.

These effects can be made use of in various combinations in order to achieve the above-mentioned aim of a pronounced and sharp artifact.

Here, one possibility is to realize the core with a central compound element or to arrange the compound element close to the center of the medical device. This would have the effect that only a comparably small layer of the surrounding water molecules is under the influence of the iron particles in the compound element, as compared to a thicker layer if the marker particles are arranged in peripheral compound elements close to the outer side of the core or even on the surface of the medical device. The thicker the layer of the affected water molecules, the wider is the resultant artifact and the image of the medical device, which then may show a larger multiple of its actual diameter. In the case of a medical device in which the core comprises a central compound element which contains the MRT marker particles, a sufficiently intense and sharp artifact is obtained, so that the image has a diameter which is only slightly larger than the actual diameter of the medical device.

This design of the medical device is based on the influence of the magnetic field, caused by the marker particles, on the protons in the water molecules which are situated in the direct vicinity of the medical device.

Another way to obtain a sharp artifact which is circumscribed very well and locally limited, is the setting of the MR sequence. If the relaxation echoes are detected which originate from the protons in a cladding matrix formed from a soft polymer and not those in the surrounding water molecules, it is possible to obtain a very sharp image which is circumscribed virtually only by the actual diameter of the core. This is preferred if it is required to position the distal end of a medical device in a narrow target area, for instance in areas which are affected by cancer. Hard polymer materials such as epoxy resins or polyurethane or thermoplastic elastomers formed from SEBS comprise a multitude of protons, but the relaxation periods for these protons are far too short in hard polymers due to the stiffness of the materials so as to detect these with currently available MR sequences and scanners. Instead of these relatively hard polymer materials, softer polymer materials may also be used as a cladding matrix for the core. With softer polymers, the protons are somewhat more flexible and exhibit longer relaxation periods. Accordingly, they can be detected with currently available MR scanners and MR sequence software. PVC or rubber is suitable for this purpose, for instance. Rubber materials exhibit a high stability because of their cross-linked polymer chains, but the protons of rubber materials still have a very long relaxation period.

Within the scope of the invention, it is also possible to dope the further compound elements with markers, in particular also with other types of MRT markers or with markers which are visible in an X-ray imaging process. Moreover, the intensity and width of the artifacts can be controlled by means of the nature and concentration of the MRT markers.

It may also be expedient to provide X-ray markers in the cladding matrix which is formed in particular from PU. A suitable material for X-ray markers is barium sulfate. Another appropriate material is represented by tungsten-microparticles, preferably having a size of 1 μm to 100 μm or 1 μm to 50 μm or 1 μm to 15 μm, or tungsten-nanoparticles preferably with a size from 1 nm to 1000 nm or 10 nm to 100 nm or 40 nm to 60 nm.

According to a further aspect of the present invention, the medical devices are provided both with MRT markers and X-ray markers, which is also described in WO 2009/141165 to which reference is made to its full extend. Preferably, the MRT markers used are passive-negative MRT markers. Passive-negative MRT markers are paramagnetic, ferromagnetic, ferrimagnetic and antiferromagnetic metals, metal alloys and metallic compounds. They are embedded in a plastic matrix preferably as particles. The passive MRT markers are preferably the following metals or metallic compounds: Cobalt (Co), nickel (Ni), molybdenum (Mo), zirconium (Zr), Titan (Ti), manganese (Mn), rubidium (Rb), aluminum (Al), palladium (Pd), platinum (Pt), chromium (Cr) or chromium dioxide ($CrO_2$), and in particular iron (Fe) and iron oxide (FeO, $Fe_2O_3$, $Fe_3O_4$) and compounds or alloys from these metals, such as FePt for example. The concentration of the passive-negative MRT markers is to be selected such that they are visible for the desired sequences and render a good image of the medical device in at least one MRT sequence, but do not superimpose or disturb the imaging process of the surrounding body tissue.

On the other hand, possible X-ray markers are the following metals or other elements: Barium (Ba), tungsten (W), tantalum (Ta), osmium (Os), praseodymium (Pr), platinum (Pt), gold (Au) and lead (Pb). These elements can be used as X-ray markers in elemental form or also in compounds such as barium sulfate, for example.

As a rule, the X-ray markers hardly have any influence on the imaging process in a magnetic resonance tomography process. However, they are clearly visible in X-ray examinations, e.g. in computer tomography or fluoroscopy processes by means of X-rays.

Some markers basically can be used both as X-ray markers and passive-negative MRT markers, with the imaging function depending on the respective concentration. As will be explained in more detail below, iron produces image signals both in magnetic resonance tomography and an X-ray examination. However, the iron concentrations required for the X-ray examination are so high that the image in the magnetic resonance tomography is disturbed here. Any markers which are usable both as X-ray markers and as MRT markers, are used in such a concentration that they neither interfere with the magnetic resonance tomography nor with the X-ray examination. As a rule, the concentration of these markers is adjusted such that they produce an image signal only in magnetic resonance tomography and are hardly visible during an X-ray examination. For platinum, there is a similar situation, but here the difference in the effect of the two imaging methods is not so pronounced.

The X-ray marker is formed from particles which are embedded in a compound element or a rod-shaped body. The rod-shaped compound element in turn is part of the medical device which may comprise several of such rod-shaped compound elements which may be provided with the same or also different MRT markers, including passive-negative MRT markers. Such a rod-shaped compound element is preferably designed as it is described as a rod-shaped body in WO 2007/000148 A2. In this respect, reference is made explicitly to this document.

The rod-shaped compound element is designed so as to have a low electrical conductivity. The particles of the markers basically may have a good electrical conductivity (e.g. iron particles or platinum particles). However, they have to be provided in such a concentration that they are isolated from one another by the matrix material and at least do not constitute an electrical conductor which is longer than 15 cm and preferably not longer than 10 cm or 5 cm.

Using such rod-shaped compound elements usually having a diameter from 0.1 mm to 0.7 mm and preferably from 0.1 mm to 0.3 mm, allows for an easy manufacture of cores, with the option that the core can be easily formed with different markers by forming it from differently doped rod-shaped compound elements. The rod-shaped compound elements may be embedded in a further, superior matrix material (the cladding matrix) for building the core. For the purpose of forming a core, however, it is also possible to braid them and pot them with a matrix material and/or a cladding matrix.

A cladding matrix of this type consists of a sheathing polymer which is not reinforced by filaments. Basically, the aim is to form the cores such that they are as rigid as possible. If the cladding matrix does not have an imaging function, it is preferred that the core is formed from a single rod-shaped body without a cladding matrix, as the compound material consisting of non-metallic filaments and the matrix material has a significantly higher stiffness than the cladding matrix.

Thus, a core comprising at least one X-ray marker and at least one MR marker can be used both in an X-ray examination and in a magnetic resonance tomography examination and is clearly visible in each case without any interference with the imaging process by one of the two markers.

LIST OF REFERENCE NUMERALS 1. medical device
2. lead probe
3. proximal end portion
4. distal end portion
5. opening
6. axial direction
7. lumen
8. core
9. non-metallic filaments
10. matrix material
11. aramide fiber
12. glass fiber
13. compound element
14. cladding matrix

The invention claimed is:

1. A medical device for insertion into a human or animal body, comprising
    an elongated, tubular lead probe including a proximal end portion and a distal end portion, the proximal end of the lead probe being provided with an opening which opens into a lumen extending in the axial direction, and the distal end of the lead probe being closed,
    an elongated core,
    the core being designed in such a manner that it can be inserted into the lead probe via the opening into the lumen, characterized in that
    the core is made from non-metallic filaments which are embedded in a matrix material.

2. The medical device according to claim 1, characterized in that
    the diameter of the core amounts to approximately 60% to 98% of the diameter of the lumen of the lead probe.

3. The medical device according to claim 1, characterized in that
    the core has a higher flexural rigidity than the lead probe.

4. The medical device according to claim 1, characterized in that
    the core comprises a magnetic resonance tomography ("MRT") marker which extends over a major part of the length of the core.

5. The medical device according to claim 4, characterized in that
    the core has its distal end portion provided with an MRT marker.

6. The medical device according to claim 4, characterized in that
    the MRT marker is formed from microparticles or nanoparticles made of one of the following metals or metallic compounds: cobalt (Co), nickel (Ni), molybdenum (Mo), zirconium (Zr), titanium (Ti), manganese (Mn), rubidium (Rb), aluminum (Al), palladium (Pd), platinum (Pt), chromium (Cr) or chromium dioxide (CrO2), iron (Fe), iron oxide (FeO, Fe2O3, Fe3O4), and FePt.

7. The medical device according to claim 4, characterized in that
    the MRT markers are concentrated along the centric longitudinal axis of the core.

8. The medical device according to claim 1, characterized in that
    the core comprises X-ray markers.

9. The medical device according to claim 1, characterized in that
    the non-metallic filaments are formed from glass fibers, ceramic fibers, Dacron®, aramide, polyaramide, Kevlar®, Dyneema® and/or vegetable fibers.

10. The medical device according to claim 1, characterized in that
    the core comprises aramide fibers and glass fibers.

11. The medical device according to claim 1, characterized in that
    the core is formed from one or more elongated compound elements which are each formed from the non-metallic filaments embedded in the matrix material, and the compound element(s) being embedded in a cladding matrix.

12. The medical device according to claim 1, characterized in that
    an electrode is arranged in the proximal end portion of the lead probe, so that the medical device constitutes a cardiac pacemaker probe.

13. The medical device according to claim 1, characterized in that
    the medical device comprises a rod-shaped body which can be inserted into the lead probe instead of the core, the rod-shaped body comprising a radiation source.

14. The medical device according to claim 13, characterized in that
    the lead probe is made from a rigid material.

15. The medical device according to claim 13, characterized in that
    the lead probe is made from a flexible material.

16. A method of positioning a medical device in a human or animal body, wherein a medical device according to claim 1 is inserted into the human or animal body.

17. The method according to claim 16,
characterized in that
the flexural rigidity of the medical device is altered at least in the distal end portion by shifting the core in the lead probe.
18. The method according to claim 16,
characterized in that
the core comprises MRT markers and/or X-ray markers, whereby the position of the medical device in the human or animal body is detected by an MRT or X-ray examination during insertion of the medical device.
19. The method according to claim 16, characterized in that the medical device is used as a pacemaker probe.
20. The method according to claim 16, characterized in that the medical device is used for brachytherapy.

* * * * *